US008076950B2

(12) United States Patent
Wee (10) Patent No.: US 8,076,950 B2
(45) Date of Patent: Dec. 13, 2011

(54) METHOD AND APPARATUS FOR MEASURING THE WATER CONDUCTIVITY AND WATER VOLUME FRACTION OF A MULTIPHASE MIXTURE CONTAINING WATER

(75) Inventor: Arnstein Wee, Randaberg (NO)

(73) Assignee: Multi Phase Meters AS, Forus (NO)

( * ) Notice: Subject to any disclaimer, the term of this patent is extended or adjusted under 35 U.S.C. 154(b) by 565 days.

(21) Appl. No.: 12/063,081

(22) PCT Filed: Jul. 27, 2006

(86) PCT No.: PCT/NO2006/000286
§ 371 (c)(1),
(2), (4) Date: May 23, 2008

(87) PCT Pub. No.: WO2007/018434
PCT Pub. Date: Feb. 15, 2007

(65) Prior Publication Data
US 2008/0303534 A1 Dec. 11, 2008

(30) Foreign Application Priority Data
Aug. 11, 2005 (NO) .................................. 20053801

(51) Int. Cl.
*G01R 27/08* (2006.01)
*G01N 30/62* (2006.01)
(52) U.S. Cl. ...................................... 324/722; 73/61.61
(58) Field of Classification Search .................. 324/722, 324/637, 638, 61.61; 73/61.61
See application file for complete search history.

(56) References Cited

U.S. PATENT DOCUMENTS

| | | | | |
|---|---|---|---|---|
| 3,778,706 A * | 12/1973 | Thompson | ..................... | 324/668 |
| 4,902,961 A * | 2/1990 | De et al. | ......................... | 324/640 |
| 4,942,363 A | 7/1990 | Lowitz | | |
| 5,103,181 A | 4/1992 | Gaisford et al. | | |
| 5,341,100 A * | 8/1994 | Taylor | ........................... | 324/341 |
| 5,576,974 A | 11/1996 | Marrelli et al. | | |
| 5,677,631 A * | 10/1997 | Reittinger et al. | ............ | 324/324 |
| 5,754,055 A * | 5/1998 | McAdoo et al. | ............... | 324/636 |
| 6,831,470 B2 * | 12/2004 | Xie et al. | ........................ | 324/693 |
| 7,135,870 B2 * | 11/2006 | Mohajer et al. | ................ | 324/639 |
| 7,219,024 B2 * | 5/2007 | Gamache et al. | ................ | 702/65 |
| 2002/0032534 A1 | 3/2002 | Regier et al. | | |

FOREIGN PATENT DOCUMENTS

GB 2 313 445 A 11/1997
WO WO 2006/019311 A 2/2006

* cited by examiner

*Primary Examiner* — Jeff Natalini
(74) *Attorney, Agent, or Firm* — Frommer Lawrence & Haug LLP; Ronald R. Santucci (57) ABSTRACT

A method for determining the water conductivity and water volume fraction of a multi-component mixture of water and at least one additional liquid or gas in a pipe, the method comprising the following steps: a. electromagnetic phase measurements at least two measurement frequencies are performed between two receiving antennas located at different distances from a sending antenna, b. based on empirically determined constant(s) and the above measurements, the real and imaginary dielectric constants are determined, c. the temperature and pressure are determined d. based on the knowledge of the real and imaginary dielectric constants of the components of the fluid mixture and the result from the above steps a-c, the conductivity of the water and/or the volume fraction of water are determined. An apparatus for performing the method is also disclosed.

13 Claims, 9 Drawing Sheets

METHOD AND APPARATUS FOR MEASURING THE WATER CONDUCTIVITY AND WATER VOLUME FRACTION OF A MULTIPHASE MIXTURE CONTAINING WATER

CROSS-REFERENCE TO RELATED APPLICATIONS

This application is a 371 of PCT/NO2006/000286 filed on Jul. 27, 2006, published on Feb. 15, 2007 under publication number WO 2007/018434 A which claims priority benefits from Norwegian Patent Application No. 2005 3801 filed Aug. 11, 2005, the disclosure of which is hereby incorporated by reference.

BACKGROUND OF THE INVENTION

The present invention relates to a method and apparatus for measuring the water conductivity and water volume fraction of a multiphase mixture in a pipe. The invention is based on a measurement of the complex dielectric constant of the multiphase mixture. The complex dielectric constant is determined by measuring the wave phase constant $\beta$ of a plane electromagnetic wave propagating near the inside wall of the pipe. The measurement of $\beta$ is based on a measurement of the phase difference between two receiving antennas inside the pipe located at different distances from a third transmitting antenna. The phase measurement is performed at least two frequencies in the range between 10 Mhz and 10 Ghz.

The method and apparatus is particularly suitable for high precision measurement of the water conductivity and water volume fraction of a flowing fluid of hydrocarbons dispersed in a continuous water phase. E.g, the invention can be used to measure the volume fraction and water conductivity of a two phase oil water mixture flowing in a pipe where the oil is dispersed in a continuous water phase. Another example is to determine the water conductivity of the water phase of a multiphase mixture containing oil, gas and water, where the oil and gas is dispersed in a continuous water phase.

A flowing mixture of oil water and gas or condensate, water and gas is a common occurrence in the oil industry being a product of an unprocessed well stream. Such a well stream is often referred to as a multiphase mixture where oil, water and gas are referred to as individual phases or fractions. The conductivity of the water phase, often referred to as the salinity of the water, can affect the measurement accuracy of measurement systems used to measure characteristics of tie mixture, such as a multiphase flow meter for measurement of oil, water and gas volume and/or mass flow rates. It is therefore common for such instruments to use the conductivity or salinity of the water phase as a calibration/configuration parameter. In many cases the water conductivity is not known. E.g. the water in the flow line may be based on the commingled production of many wells with different water salinities or a well with multiple production zones where each zone has a different water salinity. In other cases sea-water, fresh water or steam may be injected into the reservoir in order to boost the production of the wells., which also has the effect of altering the salt content of the water in the reservoir and wells over time. Under such circumstances, it is often difficult or almost impossible to obtain a reliable value of the water conductivity over time. For subsea (seabed) installations it is difficult and costly to obtain a sample from the relevant location in order to analyze the conductivity of the water phase.

A multiphase flow meter utilizing the present invention is capable of measuring the conductivity and salinity of the water fraction and hence providing reliable measurements of the oil, water and gas flow rates even for wells or commingled flow lines with changing water salinity over time.

The present invention can also be used to determine the water volume fraction and water conductivity or salinity of a two phase oil water mixture where water is the continuous phase. This is a flow condition commonly occurring in hydrocarbon process plants and oil transportation pipe lines. An apparatus for measurement of the water volume fraction of an oil/water mixture is frequently referred to as a water analyzer or watercut meter. Many such instruments rely on the water conductivity as a calibration constant. In many applications the water conductivity is not known since the water in the flow line may be based on the commingled production of many wells having different water salinity. As a consequence, the water volume fraction measurement may be incorrect. A water analyzer based on the present invention will provide reliable measurements of the water volume fraction irrespectively of any change in the water conductivity.

Microwaves are widely used for measurement of composition and water salinity of a multiphase mixture. U.S. Pat. No. 4,458,524 (1984) discloses a multiphase flow meter that measures the dielectric constant (dielectric constant), density, temperature and pressure. Such device uses phase shift between two receiving antennas to determine the dielectric constant. Other techniques are further known being based on resonance frequency measurement. Examples of such techniques are disclosed in WO3/034051 and U.S. Pat. No. 6,466, 035. U.S. Pat. No. 5,103,181 describe a method based on measurement of constructive and destructive interference patterns in the pipe.

However, none of the above described methods are able to measure the complex dielectric constant such that the water salinity of the multiphase mixture can be determined.

It is well known that the complex dielectric constant of a media can be measured by measuring the phase shift and attenuation of an electromagnetic wave through the media. U.S. Pat. No. 4,902,961 describe a method for measuring complex dielectric constant based on measurement of phase shift and power attenuation. The measurement is performed at two different (fixed) frequencies, one in the X-band and the other in the S-band. Other examples can be found in NO 200 10 616 which discloses a method for measurement of the water conductivity of the continuous phase of a multiphase mixture based on a power and phase measurement at microwave frequencies, U.S. Pat. No. 5,341,100 describing a method and apparatus for measurement of fluid conductivity and hydrocarbon volume based on a measurement of phase shift and attenuation (power) of an electromagnetic wave and U.S. Pat. No. 5,107,219 describing a method and apparatus for measurement of the conductance of a fluid based on measurement of microwave energy (power/loss) and phase difference.

The main disadvantages of the above methods and apparatuses are limited accuracy and ability to sense small variations, since they rely on an accurate power or loss measurement. Accurate power and loss measurements at microwave frequencies are difficult to perform partly due to impedance mismatch, which is very common for any microwave based industrial device for measuring dielectric constant, and partly due to limitations of the electronics itself. Consequently, the limitations of the measurement electronics and standing waves due to impedance mismatches make it difficult to obtain the required accuracy, repeatability and sensitivity for accurate fraction and/or water salinity/conductivity measurements.

NO 20043470 describes a method an apparatus for determining water salinity based on phase measurement(s) only. However, this method can not be used for a flowing fluid of hydrocarbons dispersed in a continuous phase of saline water.

BRIEF SUMMARY OF THE INVENTION

The uniqueness of the present invention is the ability to provide accurate and repeatable measurements of the complex dielectric constant and its ability to sense small variations in the complex dielectric constant without the need to perform any power and/or loss measurements. Instead the complex dielectric constant is measured based on a differential measurement of phase performed at least two different frequencies. Highly accurate measurements of the complex dielectric constant can be performed since the phase is far less affected by impedance miss-matches compared to power/loss measurements. Any discrepancies in the sensor, cable and electronic measurement paths can easily be removed by using the same physical length of both paths. Hence, the present invention is far less affected by measurement distortions related to power variations in the frequency spectrum and standing waves (rippel) in the measurement electronics sensor/antenna arrangement compared to techniques based on measurement of electrical power and/or electrical loss. The measured phase is also far less affected by scatter loss (such as Rayleigh scatter) caused by scattering of the transmitted wave in the direction of travel by droplets or bubbles in the multiphase mixture. This additional scatter loss introduces an unknown measurement error to a power/loss measurement, which is a function of the measurement frequency and size of the scattering object. As a consequence, methods based on power/loss measurements are much more influenced by the flow regime within the pipe such as droplet/bubble size. The present invention is particularly suited to perform accurate measurements of the water conductivity and/or water volume fraction of a flowing fluid of hydrocarbons dispersed in a continuous water phase.

It is the purpose of this invention to overcome the above mentioned limitations of existing solutions.

It is the purpose of this invention to provide accurate measurement of the complex dielectric constant.

It is the purpose of this invention to perform accurate measurements of the salinity and/or conductivity of the water phase of a multiphase mixture.

It is the purpose of this invention to perform accurate measurements of the salinity and/or conductivity of the water phase of a multiphase mixture at annular gas concentration in the pipe.

It is the purpose of this invention to perform accurate measurements of the water volume fraction of a multiphase mixture.

It is the purpose of this invention to perform accurate measurements of the water conductivity and/or water volume fraction of a flowing fluid of hydrocarbons dispersed in a continuous water phase.

It is the purpose of this invention to perform accurate measurements of the water conductivity and/or water volume fraction of a flowing fluid of hydrocarbons dispersed in a continuous water phase where the measurements is unaffected by the bubble and droplet size of the multiphase mixture.

It is the purpose of the invention to obtain a compact mechanical device for performing the measurements.

The method according to the present invention compromises the following steps:

a. electromagnetic phase measurements at least two measurement frequencies are performed between two receiving antennas located at different distances from a sending antenna,
b. based on empirically determined constant(s) and the above measurements, the real and imaginary dielectric constants are determined,
c. the temperature and pressure are determined
d. based on the knowledge of the real and imaginary dielectric constants of the components of the fluid mixture and the result from the above steps a-c, the conductivity of the water and/or the volume fraction of water are determined.

The apparatus according to the invention is further characterized by the features as defined in the independent claim 7

Dependent claims 2-6 and 8-9 define preferred embodiments of the invention.

BRIEF DESCRIPTION OF THE SEVERAL VIEWS

The invention will be further described in the following with reference to the figures, where.

DETAILED DESCRIPTION OF THE INVENTION

Figure 1:
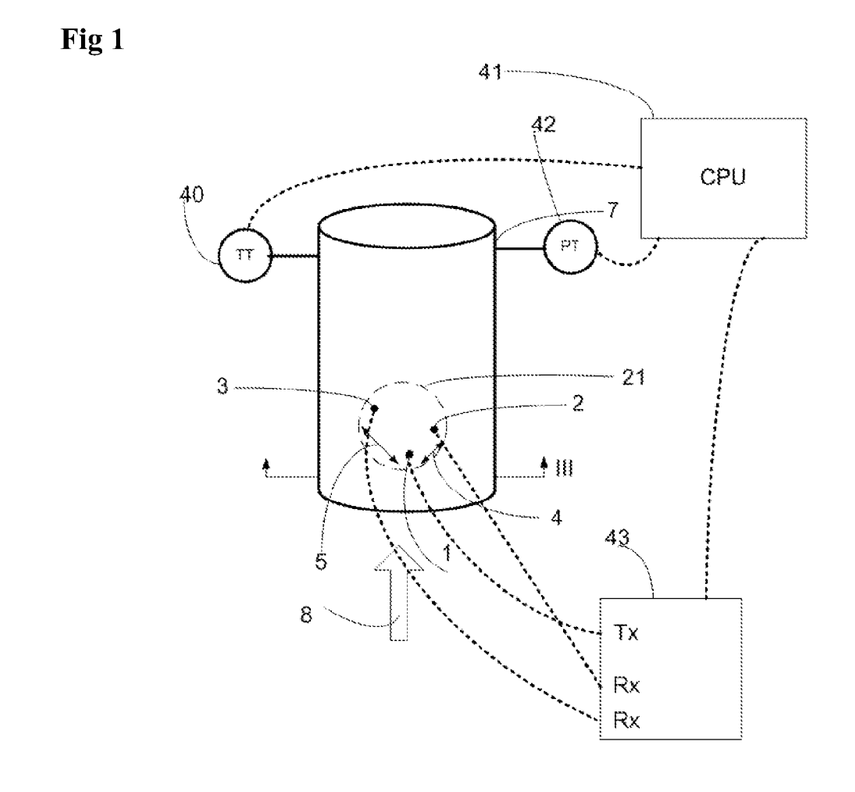
FIG. 1 shows a schematic longitudinal sectional view of an exemplified embodiment of an apparatus for measuring the water volume fraction and water conductivity according to the invention.
Figure 2:
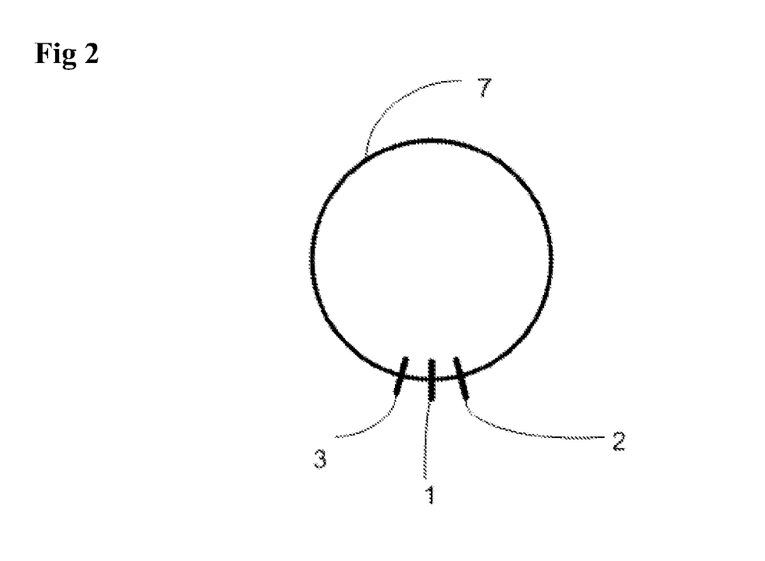
FIG. 2 shows a schematic cross sectional view along the line III-III in FIG. 1.
Figure 3:
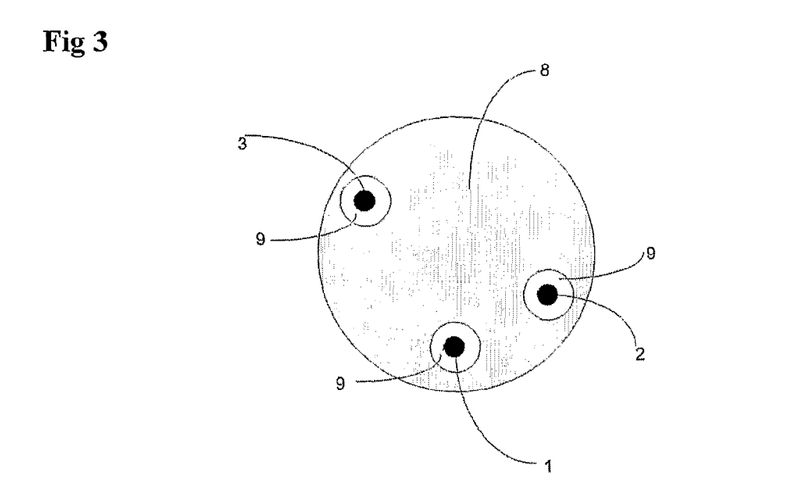
FIG. 3 shows a schematic view of a compact mechanical unit of the antennas (probe assembly)

Below is a summary of the main elements involved in determining the conductivity of the water and the water volume fraction of the multiphase mixture.
1) A sending antenna 1 and two receiving antennas 2 and 3 penetrate slightly into the pipe as shown in FIG. 2. The two receiving antennas 2 and 3 are located at distances d$_i$ 4 and d$_2$ 5 from the transmitting antenna 1. The antennas 1, 2 and 3 can be made as one unit 21, resembling a compact measurement probe, as shown in FIG. 3. The phase difference between the antennas 2 and 3 are measured for at least two frequencies transmitted on the sending antenna 1. Provided that there is sufficient loss inside the pipe at the area close to the antennas, the propagating electromagnetic wave between the sending antenna 1 and receiving antennas 2 and 3 will behave according to plane wave theory. Based on a phase measurement at at least two frequencies, the real and imaginary parts of the complex dielectric constant of the fluid within the pipe can be determined for at least two different values of the complex dielectric constant of water since the complex dielectric constant of water is also a function of the measurement frequency. FIG. 1 shows a device 43 for performing the electromagnetic phase measurements between the antennas 1-3 and transmitting the results to a computer 41. A temperature transmitter 40 and a pressure transmitter 42 are also shown, their signals likewise going to the computer 41.
2) Based on a determination of temperature and pressure and knowledge of the complex dielectric constant of water and hydrocarbon, the water fraction is calculated for all measurement frequencies for a wide range of possible water conductivities.
3) The value of the water conductivity that provides the same water volume function measurement for all measurement frequencies of pt. 2 is determined, and is a measure of the conductivity of the water within the pipe.
4) The mean water volume fraction measurement for all measurement frequencies is calculated using the water conductivity value obtained in pt. 3. This represents a measure of the water volume fraction within the pipe.

The fundamentals of electromagnetic waves traveling in a lossy media is well described in the literature (e.g. *Fields and Waves in Communication Electronics* by S. Ramo, J. R. Whinnery and T. V. Duzer) The general equation for the electric field of a positively traveling electromagnetic wave with x and y components of the electric field traveling in the direction z can be described by the following equation:

$$E = (\hat{x}E_1 + \hat{y}E_2 e^{j\psi})e^{-jkz} \qquad \text{Equation 1}$$

where:
E=Electric field vector
$E_1$=Electric field in x direction
$E_2$=Electric field in y direction
$\psi$=Phase angle between x and y component
k=Phase constant or wave number For an electromagnetic wave traveling in a lossy medium such as a mixture of oil and/or gas dispersed in water, the wave number k becomes a complex number as shown in equation 2 below.

$$k = \alpha + j\beta \qquad \text{Equation 2}$$

where:
$\alpha$=Wave attenuation coefficient
$\beta$=Wave phase constant

The exponential propagation factor for phasor waves, $e^{-jkz}$, of equation 1 then becomes, $$e^{-jkz} = e^{-\alpha z}e^{-j\beta z} \qquad \text{Equation 3}$$

Where $\alpha$ and $\beta$ can be calculated according to equation 4 and 5 below:

$$\alpha = \omega\sqrt{\left(\frac{\mu\varepsilon'}{2}\right)\left[\sqrt{1+\left(\frac{\varepsilon''}{\varepsilon'}\right)^2}-1\right]} \qquad \text{Equation 4}$$

$$\beta = \omega\sqrt{\left(\frac{\mu\varepsilon'}{2}\right)\left[\sqrt{1+\left(\frac{\varepsilon''}{\varepsilon'}\right)^2}+1\right]} \qquad \text{Equation 5}$$

where:
$\in'$=Real part of the complex dielectric constant for the media
$\in''$=Imaginary part of the complex dielectric constant for the media
$\omega$=Frequency
$\mu$=Permeability of the media, where complex dielectric constant $\in$ of the media can be described according to equation 6 below:

$$\in = \in' - j\in'' \qquad \text{Equation 6}$$

For air, gas, oil and condensate, the imaginary part of the dielectric constant is for all practical purposes zero. For water, the complex dielectric constant can be described by a single Debye relaxation law as shown below:

$$\varepsilon_{water} = \varepsilon_\infty + \frac{\varepsilon_s - \varepsilon_\infty}{1+j\omega\tau} - j\frac{\sigma_{water}}{\omega\varepsilon_0} \qquad \text{Equation 7}$$

where:
$\in_{water}$=Complex dielectric constant of water
$\in_\infty$=Dielectric constant at infinite frequencies
$\in_s$=Static dielectric constant
$\omega$=Frequency
$\sigma_{water}$=Conductivity of water
$\in_0$=Boltzmann's constant Equation 7 can be re-arranged for calculation of the real ($\in'$) and imaginary ($\in''$) part of the dielectric constant of water as shown in equation 8 and 9 below:

$$\varepsilon' = \frac{\varepsilon_s - \varepsilon_\infty}{1+(\omega\tau)^2} \qquad \text{Equation 8}$$

$$\varepsilon'' = \frac{\varepsilon_s - \varepsilon_\infty}{1+(\omega\tau)^2}(\omega\tau) + \frac{\sigma_{water}}{\omega\varepsilon_0} \qquad \text{Equation 9}$$

where:
$\in_s$=Static dielectric constant
$\in_\infty$=Dielectric constant at infinite frequency
$\sigma_{water}$=Conductivity of water
$\tau$=Dipole relaxation time
$\omega$=Frequency
$\in_0$=Boltzmann's constant Measurements and equations of the static dielectric constant of water, the dipole is relaxation time and dielectric constant at infinite frequencies are well described in the literature. Some examples can be found in J. B. Hasted which has performed a critical review of available data in *Aqueous Dielectrics* (1973). More recent data has been published by Udo Kaatze in *J. Chem. Eng. Data*, 1989 p371-374 and Meissner and Wentz in *Report from Boeing/AER investigation for CMIS*.

There is also evidence that the static dielectric constant of water, the dipole relaxation time and the dielectric constant at infinite frequencies also are dependent of the salinity of the water. The static dielectric constant of water, the dipole relaxation time and the dielectric constant at infinite frequencies for fresh water can then be multiplied by a water salinity dependent correction factor in order to obtain the values of $\in_s$, $\in_\infty$ and $\tau$ for saline water. Some examples of the equations for the water salinity correction factor for $\in_s$, $\in_\infty$ and $\tau$ has been published by Meissner and Wentz in *Report from Boeing/AER investigation for CMIS page* 17 and in J. B. Hasted, *Aqueous Dielectrics* (1973).

Figure 4:
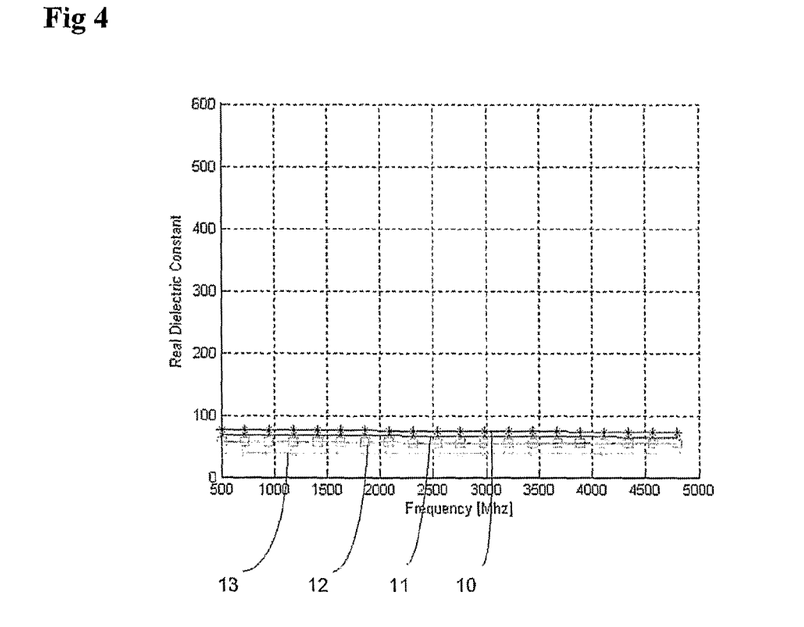
FIG. 4 shows a graph of the real part of the dielectric constant for water.
Figure 5:
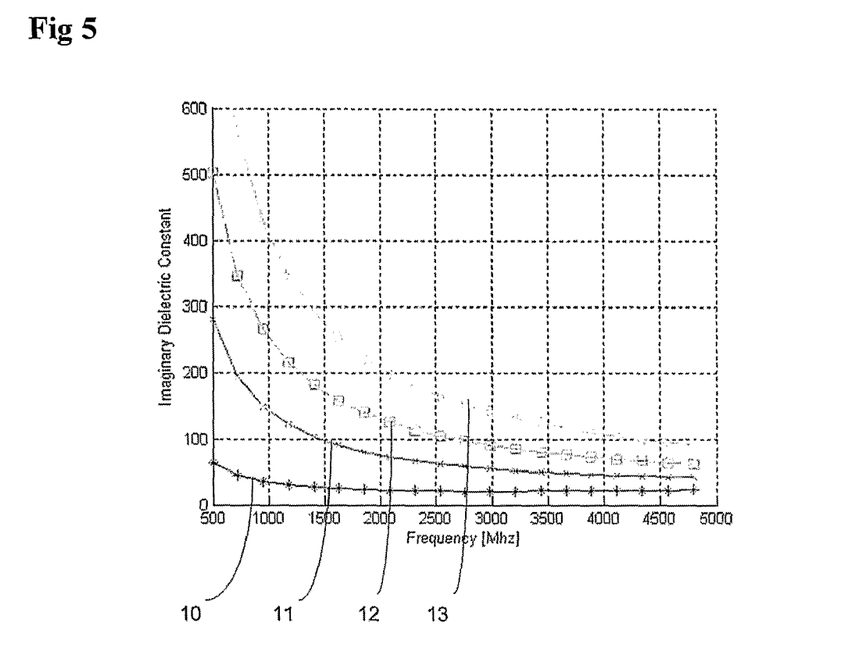
FIG. 5 shows a graph of the imaginary part of the dielectric constant for water.

FIG. 4 shows a graph of the real part of the dielectric constant for saline water (NaCl salt) at 25° C. according to equation 8 with a salinity of 1%, 5%, 10% and 20% NaCl by weight 10 11 12 13. FIG. 6 shows a graph of the imaginary part of the dielectric constant for saline water at 25° C. according to equation 9 with a salinity of 1%, 5%, 10% and 20% NaCl by weight 10 11 12 13 plotted on the same scale as FIG. 4. By comparing FIGS. 4 and 5 it is clear that the value of imaginary part of the dielectric constant of saline water is much more affected by a change in the salinity or frequency compared to the real part of the dielectric constant.

The effective real part of the complex dielectric constant is:

$$\varepsilon_{eff} = \frac{\varepsilon'}{2} * \left\{ 1 + \sqrt{1 + \left(\frac{\varepsilon''}{\varepsilon'}\right)^2} \right\} \quad \text{Equation 10}$$

where:
$\in'$: Real part of dielectric constant
$\in''$: Imaginary part of dielectric constant In mixture models the dielectric permittivity of a multiphase mixture is expressed in terms of the effective real part of the dielectric constant of every constituting component and their volume fraction. Several comprehensive reviews of dielectric mixture models have been published in the literature (van Beek, 1967; Ting a at al., 1973; Wang & Schmugge, 1980; Shutko & Reutov, 1982; Hallikainen et al., 1985; Sihlova, 1989). The Hanai-Bruggeman equation, originally derived by Bruggeman (1935) and later modified to yield complex dielectric constants by Hanai (1936), relates the dielectric constant of a two component mixture to the volume fractions of the components. If the two component mixture is droplets as an inner phase dispersed in a continuous media of an outer phase, the equation become:

$$\frac{\varepsilon_{inner} - \varepsilon_{mix}}{\varepsilon_{inner} - \varepsilon_{outer}} * \left(\frac{\varepsilon_{outer}}{\varepsilon_{mix}}\right)^{\frac{1}{3}} = 1 - \frac{\Phi_{inner}}{\Phi_{inner} + \Phi_{outer}} \quad \text{Equation 11}$$

where:
$\in_{inner}$=Dielectric constant of the inner phase (dispersed phase)
$\in_{outer}$=Dielectric constant of the outer phase (continuous phase)
$\in_{mix}$=Measured dielectric constant of the mixture
$\Phi_{inner}$=Volume fraction of inner phase (dispersed phase)
$\Phi_{outer}$=Volume fraction of outer phase (continuous phase)

Hence, by measuring the dielectric constant of a multiphase mixture and knowing the effective dielectric constant of the individual components of the mixture such as water and hydrocarbon, the, volume fraction of water and hydrocarbon can be calculated.

The dielectric constant of water is, amongst other, a function of the water conductivity and measurement frequency. However, since the water fraction is independent of both water conductivity and measurement frequency, the water conductivity can be determined by performing a water fraction measurement at least two different measurement frequencies and adjusting the water conductivity of equation 9 until the water fraction calculated according to equation 11 gives the same value at all measurement frequencies.

One way to obtain a water fraction measurement that can be performed at any pre-determined frequency is to use an apparatus as shown in FIG. 1.

Figure 11:
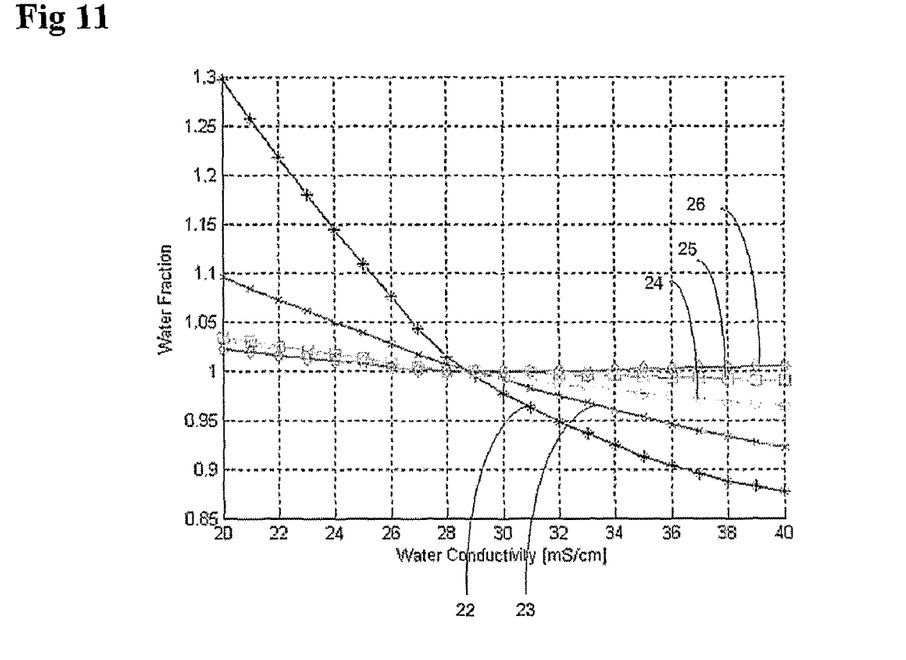
FIG. 11 shows a graph of the measured water fraction for a wide water conductivity range and five different measurement frequencies for a typical flowing fluid with a continuous water phase and low water salinity.
Figure 12:
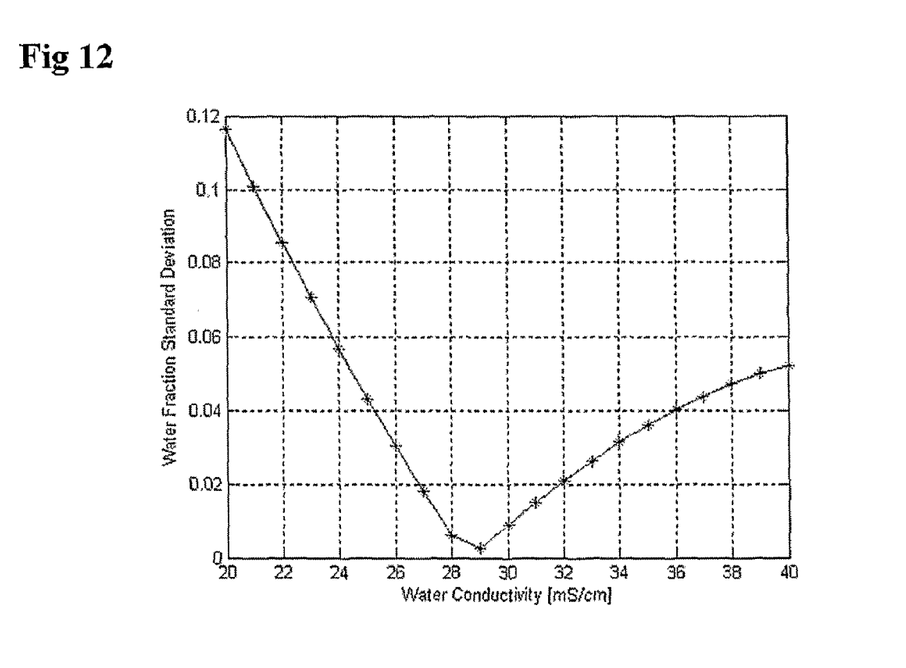
FIG. 12 shows a graph of the calculated water fraction standard deviation vs. water conductivity for the five measurement frequencies of FIG. 11.
Figure 13:
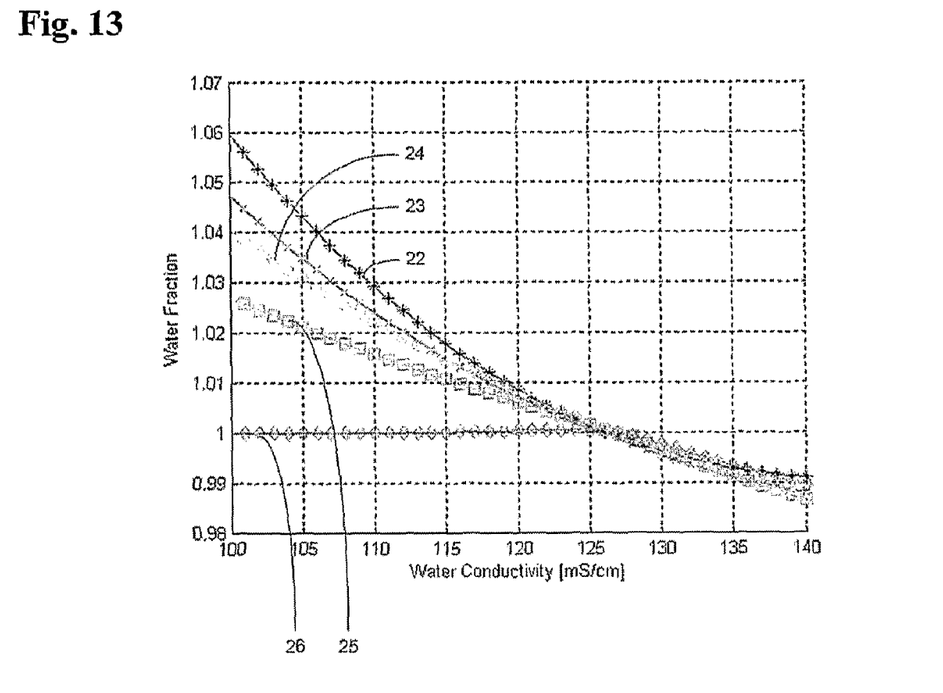
FIG. 13 shows a graph of the measured water fraction for a wide water conductivity range and five different measurement frequencies for a typical flowing fluid with a continuous water phase and high water salinity.

The apparatus containing a pipe 7 with a flowing fluid containing water and hydrocarbons. The flow direction is indicated with an arrow 8. Temperature and pressure 40, 42 are measured for compensation purposes but for the remaining discussion these measurements are ignored. A sending antenna 1 and two receiving antennas 2 and 3 penetrate slightly into the pipe as shown in FIG. 2. The two receiving antennas 2 and 3 are located at distances $d_1$ 4 and $d_2$ 5 from the transmitting antenna 1. The antennas 1, 2 and 3 can be made as one unit 21, resembling a compact measurement probe, as shown in FIG. 3. The antennas 1, 2 and 3 can be molded into a dielectric 9 such as a glass filled ceramic mold. Optimum dimension of $d_1$ are in the range 8-12 mm and for $d_2$ optimum dimension will typical be twice the dimension of $d_1$. Typical the antennas will penetrate a few mm into the pipe. The phase difference between the antennas 2 and 3 is measured for at least two frequencies transmitted on the sending antenna 1. The frequencies should also be selected such that there is sufficient difference in the imaginary part of the dielectric constant between the highest and lowest frequency such that the slope of the water fraction measurement vs. conductivity curve, as shown in FIGS. 11 and 13, differs sufficient to obtain the required sensitivity on the water fraction standard deviation calculation of FIGS. 12 and 14. The frequencies are typical selected in the range 500-5.000 Mhz, however frequencies in the range 10 Mhz to 10 Ghz may be used. The ratio between the lowest and highest frequency will be dependent of the choice of measurement frequencies and capabilities of the measurement electronics. For most application a ratio of two between the highest and lowest frequency would be sufficient when the difference between the frequencies is greater than 2 Ghz. However, adding more frequencies significantly improves the accuracy of the measured water conductivity and water fraction. Provided that there is sufficient loss inside the pipe at the area close to the antennas, the propagating electromagnetic wave between the sending antenna 1 and receiving antennas 2 and 3 will behave according to plane wave theory. In this context, sufficient loss will typical imply a water continuous multiphase mixture where the conductivity of the water at the given temperature is above approximately 7 mS/cm. A conducting water film along the pipe wall, which frequently occurs in wet gas wells, may also provide sufficient loss such that the propagating wave between the transmitting and receiving antennas behave according to plane wave theory.

According to plane wave theory, the phase difference between the receiving antennas 2 and 3 can be described as:

$$\Delta\phi = \beta * k_1 \quad \text{Equation 12}$$

where:
Δφ=Phase difference between receiving antennas 2 and 3
β=Propagating wave phase constant (ref. equation 5)
$k_1 = d_2 - d_1$
$d_1$=Distance from sending antenna 1 to receiving antenna 2
$d_2$=Distance from sending antenna 1 to receiving antenna 3

By measuring the phase difference Δφ and knowing the value of $k_1$ for the system, the phase constant β for the wave propagating from the sending to the receiving antennas can be determined. Since β also is a function of frequency (ω), χ may be a more convenient measurement parameter, which for the purpose of this patent application is defined as:

$$\chi = \frac{\beta}{\omega} \quad \text{Equation 13}$$

where:
β=Propagating wave phase constant (ref. equation 5)
ω=frequency (rad)

χ can then be calculated from the measured phase difference, measurement frequency and value of $k_1$ according to equation 14 below:

$$\chi = \frac{\Delta\varphi}{k_1 \omega} \quad \text{Equation 14}$$

Combining equation 5, 12, 13 and 14 provides the following equation for the real (∈') and imaginary (∈") part of the dielectric constant within the pipe.

$$\chi = \sqrt{\left(\frac{\mu\varepsilon'}{2}\right)\left[\sqrt{1+\left(\frac{\varepsilon''}{\varepsilon'}\right)^2}+1\right]} \quad \text{Equation 15}$$

Figure 6:
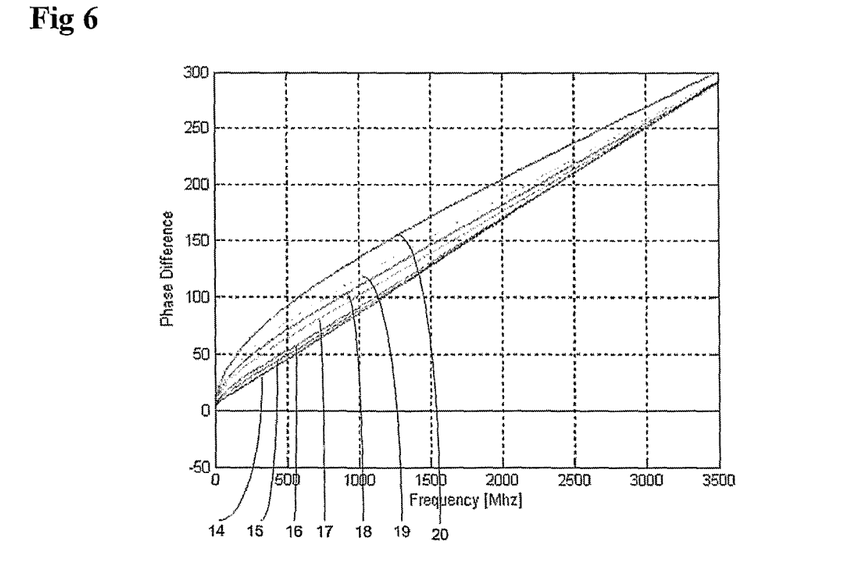
FIG. 6 shows a graph of theoretical phase vs. frequency response for the apparatus.

FIG. 6 shows the theoretical phase difference at the receiving antennas for a plane wave traveling from the sending antenna to the receiving antennas for $k_1$=0.008. The phase difference is calculated in a frequency range from 0.1 to 3.500 Mhz with a water fraction of 1.0 and a water salinity of 1%, 1.75%, 2.5%, 5%, 7%, 9% and 15% salt (NaCl) by weight shown by curves 14, 15, 16, 17, 18, 19, 20, respectively.

Figure 7:
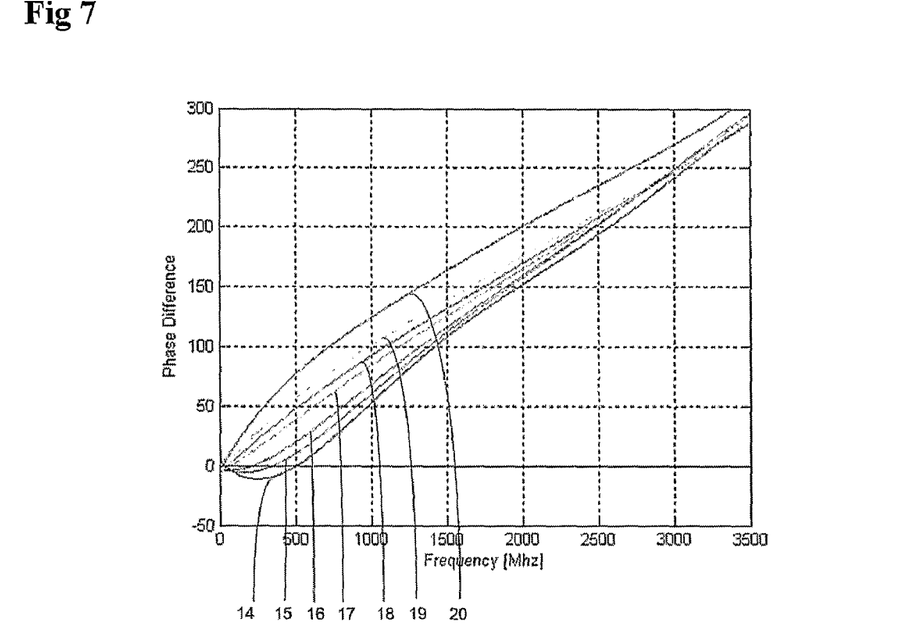
FIG. 7 shows a graph of the measured phase vs. frequency response for the apparatus.

FIG. 7 shows the corresponding measured phase difference of the apparatus of FIG. 1 with corresponding values for $k_1$ and water salinity.

Figure 8:
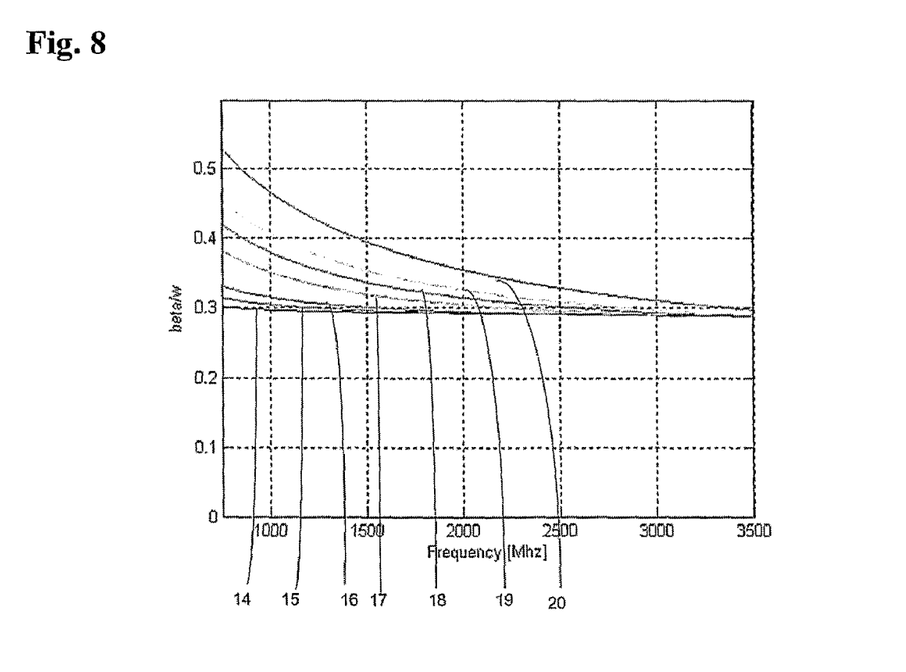
FIG. 8 shows a graph of the theoretical value of $\beta/\omega$ vs. frequency for the apparatus.
Figure 9:
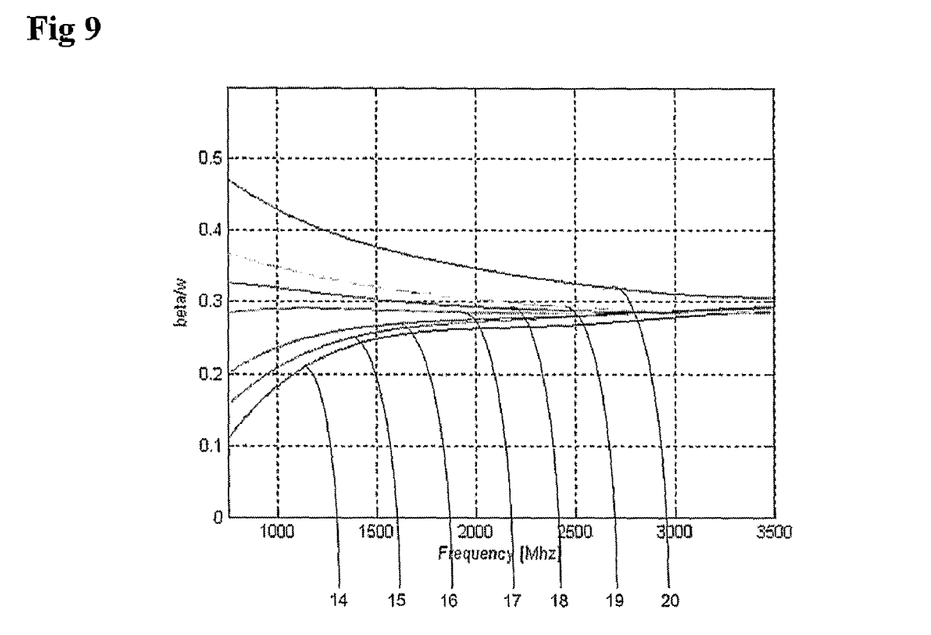
FIG. 9 shows a graph of the measured value of $\beta/\omega$ vs. frequency for the apparatus.

FIG. 8 shows the theoretical value of χ (i.e. beta/ω) for a frequency range of 750 Mhz-3.500 Mhz with a water salinity of 1%, 1.75%, 2.5%, 5%, 7%, 9% and 15% salt (NaCl) by weight shown by curves 14, 15, 16, 17, 18, 19, 20, and FIG. 9 shows the corresponding measured value of χ for the apparatus of FIG. 1 with corresponding values for $k_1$ and water salinity.

As seen from FIGS. 7 and 8 the theoretical and measured values and agrees well at frequencies above say 2,000 Mhz for all the water salinities and more or less over the entire frequency range for higher water salinities. For lower salinities of water and when the measurement frequency is reduced below 2,000 Mhz, the measured value of χ deviates from the theoretical value of χ assuming plane wave propagation between the transmitting and receiving antenna. This discrepancy is due to the wave-guide mode within the pipe violating the assumption regarding pure plane wave propagation is between the sending and receiving antennas and a small distance between the transmitting and receiving antennas such that the receiving antennas in effect are located in the near field from the transmitter antenna.

However, the discrepancy between the theoretical and measured value of χ can be corrected by using a water salinity or conductivity dependent correction factor (Multiplication Factor). The salinity/conductivity dependent Multiplication Factor can be derived empirically by measuring the phase difference vs. frequency for a variety of water samples with a known water conductivity/salinity as exemplified below.

Figure 10:
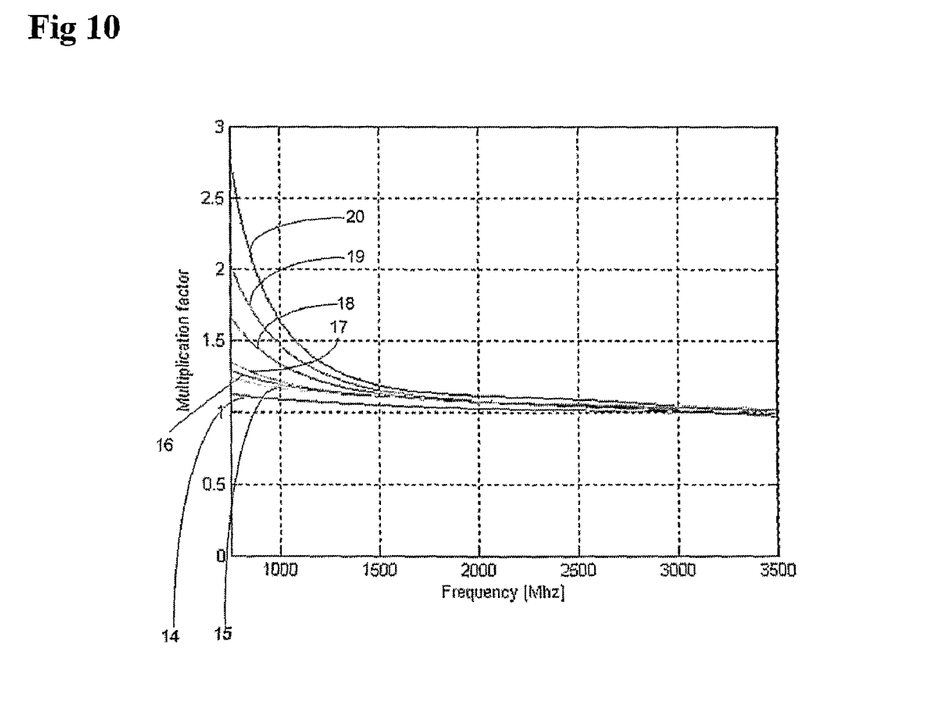
FIG. 10 shows a graph of the empirically derived correction factor (Multiplication Factor) for the apparatus.

FIG. 10 shows a graph of the correction factor (Multiplication factor) obtained by dividing the measured values by the theoretical values of χ for water salinities of 1%, 1.75%, 2.5%, 5%, 7%, 9% and 15% salt (NaCl) by weight shown by curves 14, 15, 16, 17, 18, 19, 20 and a frequency range of 750 Mhz to 3,500 Mhz. The correction factor is a function of frequency and water salinity, and can be derived for any combination of frequency and water conductivity simply be interpolating between the graphs.

Using the Multiplication Factor to correct the measurement, the measured value of χ then becomes:

$$\chi = M(\omega, \sigma_{water}) * \frac{\Delta\varphi}{k_1 \omega} \quad \text{Equation 16}$$

where:
$M(\omega, \sigma_{water})$=Frequency and water conductivity dependent Multiplication Factor
Δφ=Measured phase difference between receiving antennas 2 and 3
$k_1 = d_2 - d_1$
$d_1$=Distance from sending antenna 1 to receiving antenna 2
$d_2$=Distance from sending antenna 1 to receiving antenna 3
ω=Measurement Frequency (rad)

The steps involved in order to determine the water conductivity and water (volume) fraction are listed below, ignoring the steps involved in temperature and pressure compensating the measurements:

1) Measure phase difference Δφ at a pre-determined frequency ω
2) Assume a water conductivity $\sigma_{water}$ of $\sigma_1$
3) Calculate Multiplication Factor $M(\omega, \sigma_{water})$
4) Calculate χ according to equation 16
5) Calculate imaginary part of dielectric constant (∈") of the media inside the pipe according to equation 9
6) Calculate real part of the dielectric constant (∈') of the media inside the pipe according to equation 15
7) Calculate the measured effective dielectric constant of the media inside the pipe ($\in_{eff}$) according to equation 10
8) Calculate the volume fraction of water according to equation 11 where inner phase is hydrocarbons, outer phase is water and measured dielectric constant is the effective dielectric constant calculated in step 7 above.
9) Repeat step 2-8 for a wide range of water conductivities ($\sigma_2, \sigma_3, \sigma_4, \ldots$). The water conductivity is typical varied from the lowest expected water conductivity to the highest expected water conductivity for the fluid flowing in the pipe in steps of say 1-5 mS/cm 10) Repeat step 1-9 for other measurement frequency or frequencies FIG. 11 shows the resulting water fraction calculation vs. water conductivity for 5 different measurement frequencies calculated according to steps 1-10 at a step size of 1 mS/cm for a water conductivity of 29.1 mS/cm and water fraction of 1.0 inside the pipe. The measurement frequencies used in this case are 800 Mhz, 1100 Mhz, 1500 Mhz, 2100 Mhz and 3400 Mhz respectively 22 23 24 25 and 26. From the graph of FIG. 12 it is seen that the water fraction measurement has a different slope vs. water to conductivity for the various measurement frequencies, and the water fraction measurements intercept at a water conductivity value around 29 mS/cm. I.e. for a water conductivity of 29 mS/cm the water fraction measurement is the same for all the measurement frequencies which again provides a measurement of the water fraction and water conductivity. Statistically methods can also be used to determine the point of interception or the point where the spread of the water fraction measurements are at a minimum value. E.g, by calculating the standard deviation between the water fraction measurements at each value of the water conductivity, a curve as shown in FIG. 12 can be derived. FIG. 12 shows a graph of the calculated standard deviation between the calculated water fractions for all the measurement frequencies. As seen on FIG. 12, this graph has a minima around 29 mS/cm corresponding to the conductivity of tie water. One way to determine the location of the minima of the graph of FIG. 12 is to apply a curve fit (such as a $5^{th}$ order polynomial curve fit) to the calculated standard deviation vs. water conductivity and using a computer to numerical find the minima of the curve fitted function.

Figure 14:
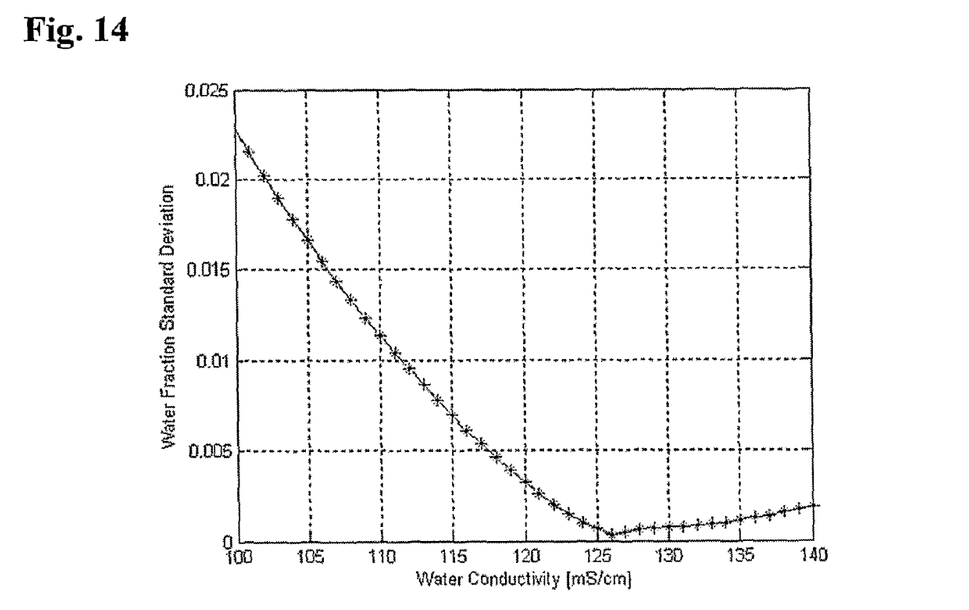
FIG. 14 shows a graph of the calculated water fraction standard deviation vs. water conductivity for the five measurement frequencies of FIG. 13.
Figure 15:
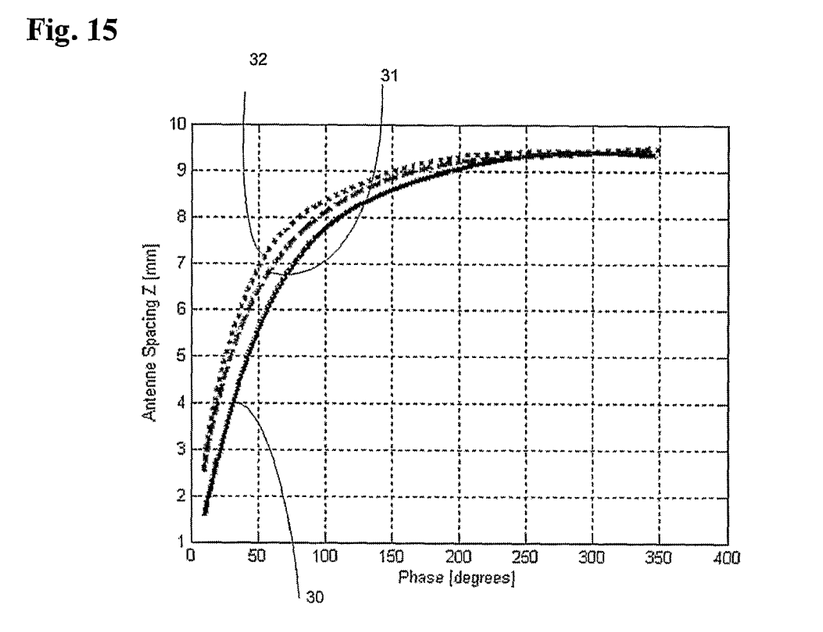
FIG. 15 shows a graph of the calibration factor Z vs. phase for the apparatus.

FIGS. 13 and 14 shows the measured water fraction vs. water conductivity for a water conductivity of 127.4 mS/cm (FIG. 13) and the calculated standard deviation of the water fraction measurements vs. water conductivity (FIG. 14). As seen on FIG. 14, the graph has a minima around 127 mS/cm. FIG. 15 shows the measured water conductivity for a range of water conductivities.

Based on the above discussion, the following additional steps are involved in determining the water conductivity and water (volume) fraction:

11) Determine the conductivity value for the point of interception between the various water fraction calculations, alternatively determine the conductivity value for the minima point of the water fraction standard deviation curve vs. water conductivity. This conductivity value is a measure of the conductivity of the water of the multiphase mixture
12) Calculate the mean value of the water fraction measurement of all the measurement frequencies and the water conductivity of step 11. The water fraction calculation can be performed according to step 1-10 above using the water conductivity determined in step 11. The mean value for the water fraction is a measure of the water fraction of the multiphase mixture A somewhat simpler way to calibrate the measurement has been found by using a phase dependent calibration factor Z as the effective antenna distance substituting the calibration constant $k_1$ of equation 12. This is due to the fact that the effective antenna distance Z is a function of the transmitted wavelength, which again is a function of the measured phase difference between the two receiving antennas. The effective distance Z is also dependent on the multiphase conductivity and Z can then be calculated as shown below:

$$Z = f(\Delta\phi, \sigma_{mix}) \quad \text{Equation 17}$$

where:

Z: Effective antenna distance (calibration constant)
$\Delta\phi$: Measured phase difference
$\sigma_{mix}$: Conductivity of the multiphase mixture Examples of such functions are shown in FIG. 15 with water salinity of 0.47%, 5.21%, and 16.08% by weight shown by curves 30, 31, 32, respectively. The appropriate curve is selected based on the measured water conductivity and the measured phase difference defines the point on the curve. Interpolation between the curves can be used for intermediate conductivities. The above curves can be obtained empirically by filling the sensor with saline water with known water conductivity and measuring the phase vs. frequency over a desired frequency range.

The conductivity of the oil/water mixture can be calculated according to the Maxwell Garnett mixing formula as shown below:

$$\sigma_{mix} = \sigma_{water} + 3*\Phi_{oil}*\sigma_{water}*\frac{\sigma_{oil}-\sigma_{water}}{\sigma_{oil}-2*\sigma_{water}-\Phi_{oil}*(\sigma_{oil}-\sigma_{water})} \quad \text{Equation 18}$$

where:

$\sigma_{mix}$: Conductivity of the oil water mixture
$\sigma_{oil}$: Conductivity of the oil
$\sigma_{water}$: Conductivity of the water
$\Phi_{oil}$: Fraction of oil in the liquid phase The complex dielectric constant can be determined in an iterative calculation loop. Assuming a constant ratio between the real and imaginary part of the dielectric constant when performing these iterations simplifies the calculations. Experiments have shown that the ratio between the real and imaginary dielectric constant for pure water applied to a mixture of water and oil, provides accurate calculations of the volume fraction. This approximation introduces only small measurement errors since the Bruggeman mixing formula is fairly linear function.

Hence, the ratio between the real and imaginary dielectric constant is defined as:

$$K = \frac{\varepsilon''_{water}}{\varepsilon'_{water}} \quad \text{Equation 19}$$

The real part of the dielectric constant for the mixture can then be calculated by combining equation 19 and 5 as shown below:

$$\varepsilon' = \frac{2*\beta^2}{\omega^2*(\sqrt{1+K^2}+1)*\mu} \quad \text{Equation 20}$$

The steps involved in order to determine the water conductivity and water (volume) fraction are listed below, ignoring the steps involved in temperature and pressure compensating the measurements:

1) Measure phase difference $\Delta\phi$ at a pre-determined frequency $\omega$
2) Assume a water conductivity $\sigma_{water}$ of $\sigma_1$
3) Calculate real and imaginary dielectric constant of water according to equations 8 and 9
4) Calculate K according to equation 19
5) Calculate conductivity of the oil/water mixture based on the last calculation of the oil fraction and the conductivity of water and oil using equation 18

Figure 16:
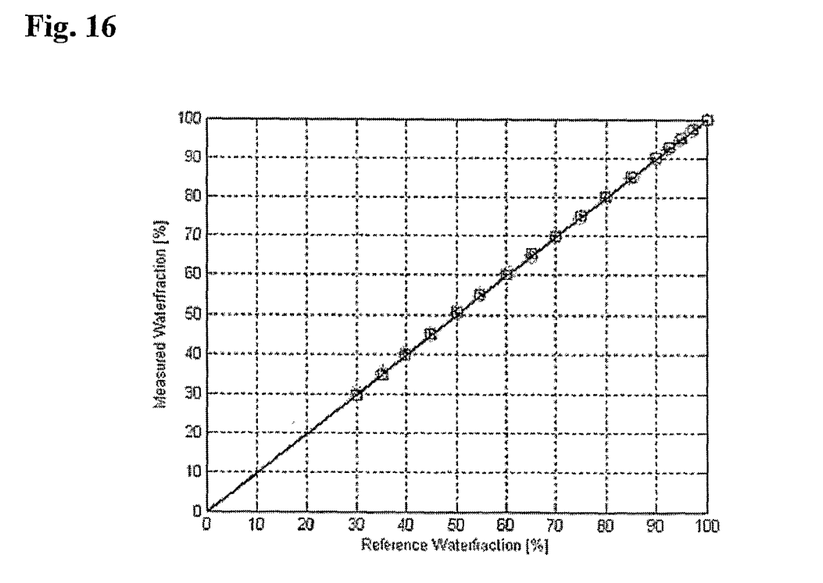
FIG. 16 shows a graph of the measured water fraction vs. the reference water fraction for salinities in the range 0.5%-25% NaCl and water fractions in the liquid phase in the range 30-100%.
Figure 17:
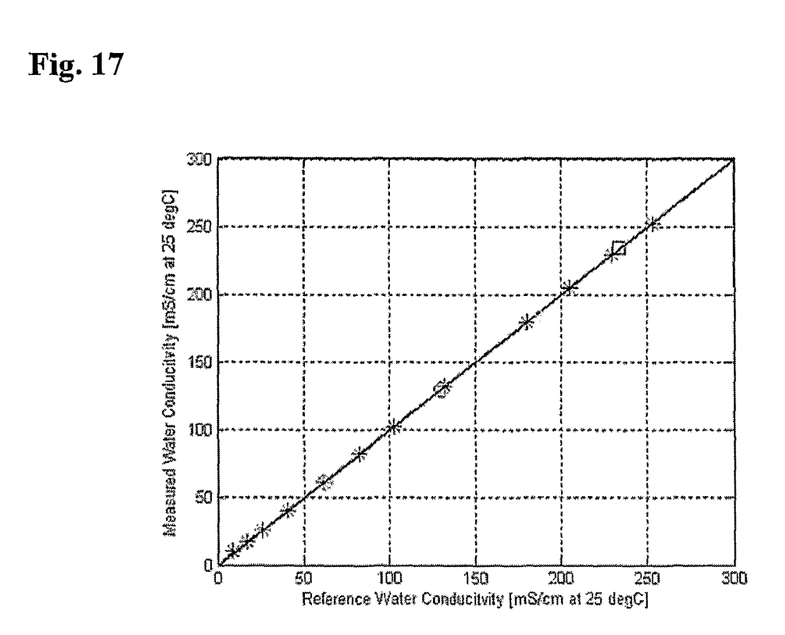
FIG. 17 shows a graph of the measured conductivity vs. the reference conductivity for salinities in the range 0.5%-25% NaCl and water fractions in the liquid phase in the range 30-100%.

6) Calculate effective antenna distance Z using equation 17
7) Calculate measured value of $\beta$ using equation 12 and substituting $k_1$ with Z
8) Calculate the real part of the dielectric constant for the oil/water mixture using equation 20
9) Calculate the imaginary and effective real part of the dielectric constant of the oil/water mixture using equation 19 (imaginary part) and 10 (effective real part)
10) Calculate the volume fraction of water based on the effective real part of the dielectric constant of water oil and the oil/water mixture using equation 11
11) Repeat steps 5-10 until the calculation of the water fraction has converged
12) Repeat steps 2-11 for next measurement frequency
13) Repeat step 2-12 for a wide range of water conductivities ($\sigma_2, \sigma_3, \sigma_4, \ldots$). The water conductivity is typical varied from the lowest expected water conductivity to the highest expected water conductivity for the fluid flowing in the pipe in steps of say 1-5 mS/cm Based on the previous discussion related to calculation of the water fraction standard deviation curve, the following additional steps are involved in determining the water conductivity and water (volume) fraction:

14) Determine the conductivity value for the point of interception between the various water fraction calculations, alternatively determine the conductivity value for the minima point of the water fraction standard deviation curve vs. water conductivity. This conductivity value is a measure of the conductivity of the water of the multiphase mixture
15) Calculate the mean value of the water fraction measurement of all the measurement frequencies and the water conductivity of step 14. The water fraction calculation can be performed according to step 1-12 above using the water conductivity determined in step 11 and the average water fraction from all frequency measurements. This average value for the water fraction is a measure of the water fraction of the multiphase mixture FIG. 16 shows a graph of the measured water fraction vs. the reference water fraction for salinities in the range 0.5%-25% NaCl and water fractions in the liquid phase in the range 30-100% and FIG. 17 shows a graph of the measured conductivity vs. the reference conductivity for salinities in the range 0,5%-25% NaCl and water fractions in the liquid phase in the range 30-100% based on the above steps.

Since the antennas are located close to the wall, the measured water conductivity and water fraction will be representative for the water fraction values and water conductivity values along the pipe wall. Since the salt in the water is well dissolved in the water, the water conductivity will be the same in the entire cross section of the pipe. For a two to phase oil/water mixture, the water fraction may be unevenly distributed in the cross section of the pipe. In order to obtain a representative measurement of the water fraction of the pipe cross section. a mixing or homogenizing device may be required upstream the measurement device.

For a multiphase fluid containing water oil and gas or water, condensate and gas in upward flowing pipe lines, there is normally a higher concentration of gas in the middle of the pipe compared to the amount of gas along the pipe wall. This effect can be referred to as annular gas concentration. In extreme cases more or less all the liquid will be distributed as a ring along the pipe wall whereas all the gas is flowing in the middle of the pipe. This occurrence is normally referred to as annular flow. In annular flow or at annular gas concentration, the water fraction measurement will not represent the water fraction in the whole cross section of the pipe, but will represent a measurement of the water fraction near the pipe wall. However, since the salt of the water is well dissolved, the water conductivity will be unaffected by liquid and gas distribution in the cross section of the pipe.

Knowing the conductivity of water, it is possible to determine the salt content of the water. Tables of conductivity vs. salt content can be found in the *CRC Handbook of Chemistry and Physics*. Algorithms for calculating the conductivity vs. salt content and temperature can be found in Robinson and Stokes, *Electrolyte Solutions* (1959) and 4.L. Horvath, *Handbook of Aqueous Electrolyte Solutions* (1985).

The present invention can be used to determine the water fraction and water conductivity or salinity of a two phase oil water mixture where water is the continuous phase commonly occurring in hydrocarbon process plants and transportation pipe lines. Many instruments for measurement of water fraction in a oil water mixture rely on the water conductivity as a calibration constant. In many applications the water conductivity is not known since the water in the flow line is based on the commingled production of many wells which may have a different water salinity. In other cases sea-water, fresh water or steam injection into the reservoir may alter the salt content of the wells over time. Since the present invention measures both the water fraction and the salinity of the water, the water fraction measurement is unaffected by any changes in the water salinity and the salinity measurement can also be used to identify the location of the produced ater from the well. E.g., when salinity of the water in the reservoir and the injected water is known, the amount of injection water and reservoir water in the produced water of the well can be determined.

The present invention can also be used to determine the water conductivity or water salinity of a multiphase mixture containing gas in addition to the water fraction near the pipe wall of a multiphase mixture containing gas. The water conductivity or water salinity is typical a calibration parameter for most multiphase meters. In many applications, particularly for subsea/seabed installations, the water conductivity may not be known due to commingled flow of multiple wells or a well with multiple production zones where each zone has different water salinity. Under such circumstances it may be difficult or almost impossible to obtain a reliable value of the water conductivity over time. Consequently, the calibration of multiphase flow meter will be wrong which could severely deteriorate the accuracy of the flow rate measurements of the flow meter. A multiphase flow meter utilizing the present invention is capable of measuring the conductivity and salinity of the water fraction and hence providing reliable measurements of the oil, water and gas flow rates even for wells o commingled flow lines with changing water salinity over time.

The invention claimed is:

1. A method for determining the water conductivity and water volume fraction of a multi-component mixture of water and further fractions of at least one non-aqueous additional liquid and a gas in a pipe, the method comprising the following steps:
   a. measure electromagnetic phase difference at at least two pre-determined frequencies in the pipe,
   b. assume a value for the conductivity of the water in the multi-component mixture,
   c. determine the pressure and temperature of the multi component mixture,
   d. calculate the real and imaginary dielectric constant of water of the mixture for the first measurement frequency based on the result from step a-c, e. calculate the ratio between the real and imaginary dielectric constant of water of the mixture obtained in the previous step, f. calculate the real part of the dielectric constant of the multi-component mixture based on the result from step a, at least one of calibration constant obtained empirically by measuring the phase vs. frequency for saline water with known water conductivity and a multiplication factor obtained empirically by measuring the phase difference vs. frequency for water samples of known water salinity, and the result from step e, g. calculate the imaginary part and effective part of the dielectric constant of the multi-component mixture based on the result from steps f and e, h. calculate the volume fraction of water of the mixture based on knowledge of the dielectric constant of the non-aqueous liquid(s), gas and the result from step d, i. repeat step d-h for the other pre-determined frequencies from step a, j. repeat step a-i for another water conductivity and repeat step b-j until the entire expected water conductivity range have been covered, and k. determine the water volume fraction of the multi-component mixture and water conductivity of the water fraction by identifying the water conductivity from step b and water fraction from step h which gives the most similar water fraction for all pre-defined measurement frequencies.

2. A method according to claim 1, wherein the multi-component mixture contains oil, gas and water.

3. A method according to claim 2, wherein the electromagnetic measurements are performed in a frequency range between 10 Mhz and 10 000 Mhz.

4. A method according to claim 2, wherein the electromagnetic phase measurements are performed near the pipe wall.

5. A method according to claim 1, wherein the electromagnetic measurements are performed in a frequency range between 10 Mhz and 10 000 Mhz.

6. A method according to claim 5, wherein the electromagnetic phase measurements are performed near the pipe wall.

7. A method according to claim 1, wherein the electromagnetic phase measurements are performed near the pipe wall.

8. A method according to claim 1, wherein the empirically determined calibration constant is a function of the conductivity of the water and/or the measurement frequency.

9. A method according to claim 1, wherein the empirically determined calibration constant is a function of the measurement phase.

10. A method according to claim 1, wherein the most similar water fraction for all pre-determine measurement frequencies is calculated based on statistical methods.

11. An apparatus for determining the water conductivity and water volume fraction of a multi-component mixture of water and further fractions of at least one non-aqueous additional liquid and a gas in a pipe, the apparatus comprising a tubular section and the following elements:

a. a computer b. means for performing electromagnetic phase difference measurements inside the pipe between two receiving antennas located at different distances from a sending antenna at at least two measurement frequencies and transmitting the result to the computer, c. means for determining the temperature of the multi-component mixture and transmitting the result to the computer, d. a program for the computer for calculating the imaginary and real part of the dielectric constant of the water in the mixture, e. means for determining the pressure of the multi-component mixture and transmitting the result to the computer, f. a program for the computer for calculating the ratio of the real and imaginary dielectric constant of the water volume fraction, g. a program for the computer for calculating the real and imaginary dielectric constant of the multi-component mixture based on at least one of a calibration constant obtained empirically by measuring the phase vs. frequency for saline water with known water conductivity and a multiplication factor obtained empirically by measuring the phase difference vs. frequency for water samples of know water salinity, and the results/data determined by the elements b-f, h. a program for the computer for calculating the water conductivity and/or the volume fraction of water of the fluid mixture based on knowledge of the real and imaginary dielectric constants of the non-aqueous components of the multi-component mixture and the results/data determined by the elements b-g.

12. An apparatus according to claim 11, wherein the tubular section comprises at least one transmitting antenna and at least two receiving antennas located in substantially the same area along the pipe wall.

13. An apparatus according to claim 11, comprising electronic means for transmitting at least two frequencies on at least one transmitting antenna at the time and recording phase difference for the frequencies at at least two receiving antennas.

* * * * *